United States Patent [19]
Padilla et al.

[11] Patent Number: 6,125,235
[45] Date of Patent: Sep. 26, 2000

[54] METHOD FOR GENERATING A REFINED STRUCTURAL MODEL OF A MOLECULE

[75] Inventors: Carlos E. Padilla, Somerville; Valeri I. Karlov, Boston, both of Mass.

[73] Assignee: Photon Research Associates, Inc., San Diego, Calif.

[21] Appl. No.: 08/872,608

[22] Filed: Jun. 10, 1997

[51] Int. Cl.[7] ........................................... G06G 7/48
[52] U.S. Cl. ........................................... 395/500.32
[58] Field of Search ........................................... 395/500.23

[56] References Cited

PUBLICATIONS

Brunger, A.T., X–PLOR (vers 3.1), A System for X–ray Crystallography and NMR. 20 NMR Structure Determination, 1992, New Haven and London: Yale University Press, pp. 295–328.
Brunger, A.T., X–PLOR (vers 3.1), A System for X–ray Crystallography and NMR,, 21 NMR Backcalculation Refinement, 1992, New Haven and London: Yale University Press, pp. 329–348.
Clore, G.M., et al., *Journal of Molecular Biology*, 1986. 191: pp. 523–551.
Delfini, D., et al., *Journal of Computational Chemistry*, 1996. 17: pp. 74–86.
Gleb, A., et al. *Applied Optimal Estimation*, 1974, Cambridge, Massachusetts, and London, England, The M.I.T. Press, pp. 107–113 and 190–191.
Jazwinsky, A.H., *Stochastic Processes and Filtering Theory*. 1970, New York: Academic Press, pp. 332–352.
Kalman, R.E., *Journal of Basic Engineering (ASME)*, 1960. 82D: pp. 35–45.
Koehl, P., et al., *Journal of Molecular Biology*, 1992. 223: pp. 299–315.
Nilges, M., et al., *FEBS Letters*, 1988. 229: pp. 317–324.
Pachter, R., et al., *Journal of Magnetic Resonance*, 1990. 90.
Pachter, R., R.B. Altman, and O. Jardetzky, *Journal of Magnetic Resonance*, 1990. 89.
Yip, P., et al., *Journal of Magnetic Resonance*, 1989. 83: pp. 643–648.
Yip, P. and D. Case, *Computational Aspects of the Study of Biological Macromolecules by NMR Spectroscopy*, 1991. New York: Plenum Press, pp. 317–330.

*Primary Examiner*—Kevin J. Teska
*Assistant Examiner*—Hugh Jones
*Attorney, Agent, or Firm*—McDermott Will & Emery

[57] ABSTRACT

A computer assisted method for generating a representation of a three dimensional structure of a molecule is described. The invention recursively filters an a priori vector of structural parameters, representative of the three dimensional structure of the molecule, based upon experimental observations relating to the structural parameters. The invention produces a refined vector of structural parameters and an associated covariance matrix indicating the accuracy of the vector. The invention includes a set of non-linear functions which implement a model relating the observations to the vector of structural parameters. The recursive steps of the method include a prediction step and an update step. During the prediction step, the non-linear model is analyzed by statistical methods. Only the results of the prediction step are incorporated in the update step, thus isolating the non-linear aspects of the model within the prediction step.

40 Claims, 5 Drawing Sheets

METHOD FOR GENERATING A REFINED STRUCTURAL MODEL OF A MOLECULE

FEDERALLY SPONSORED RESEARCH

This invention was made with government support under Grant Number 2R44GM53363-02 awarded by National Institute of Health, National Institute of General Medical Sciences. The government has certain rights in the invention.

The U.S. Government has a paid-up license in this invention and the right in limited circumstances to require the patent owner to license others on reasonable terms as provided for by the terms of Grant Number 2R44GM53363-02 awarded by National Institute of Health, National Institute of General Medical Sciences.

RELATED APPLICATIONS

Not Applicable

BACKGROUND OF THE INVENTION

The present invention relates to methods for determining and refining three dimensional structures of molecules, and more particularly a method for determining and refining three dimensional structures of molecules by non-linear recursive filtering of chemical information and structural observations.

Accurate knowledge of the three dimensional structure of macro-molecules is essential for modeling their biological functions and, thus, for structure-based drug design. Nuclear Magnetic Resonance (hereinafter referred to as NMR) technology makes it possible to measure quantitative characteristics of macro-molecules in solution. At the same time, this poses new challenges for the problem of converting the NMR data into a three dimensional structure. It is well understood that the NMR data, for example, Nuclear Overhauser Effect (hereinafter referred to as NOE) intensities have a complicated nonlinear structure arising from multiple-spin-effect, which is also known as the spin diffusion problem. Simplification of that information by attempting to un-couple spins leads to loss of accuracy. Direct refinement of the three dimensional structure by the NOE intensities poses, however, significant computational difficulties for large molecules, even within the current limit on the size of molecules accessible by NMR experiments. Also, the complexity of the measurement model is aggravated by various deficiencies in data such as experimental noise, uncertainties in the assignments of proton resonances and uncertainties in relaxation parameters and contributions from dynamical effects.

Traditionally, the problem of obtaining three dimensional structures from pre-processed experimental NMR data is divided into the distinct steps of determination and refinement. During determination, an initial family of structures is generated that approximately satisfy covalent and experimental restraints. Each member of the structural family is then refined against the experimental data to increase the final accuracy. This conceptual division is convenient due to the multiple-minima nature of a global functional representation of the optimization target for the entire structure. Historically, the algorithmic methods used during the determination step were distinct from the methods used during the refinement step. However, the dividing line can be blurred if algorithms are able to systematically handle the multiple-minima problem.

In NMR applications, the method of structure optimization is substantially defined by how the NMR data is treated.

A significant effort in determination and refinement techniques of the NMR structures is aimed at utilizing more complete information from experimental NOE intensities. The results can be split into indirect and direct approaches. The indirect approach offers better interpretation of NOE intensities in terms of distances rather than the simplest classification of distances attributed to strong, medium and weak NOE peaks. The indirect approach is usually used at both determination and refinement stages. Various methods offer ways to smooth distances by triangle bound inequalities or by more accurate, but computationally intensive, tetrangle inequalities. In the indirect approach, relaxation matrix calculations are also used to account for all magnetization transfers, also known as spin diffusion, resulting in more accurate distance representations. The target distances can be iteratively modified manually or automatically to match observed and calculated two dimensional NOE intensities. Another approach is based on the back-transformation of the matrix of intensities to obtain the relaxation matrix and hence, the cross-relaxation rates. In practice the experimental NOE matrix is incompletely known due to overlap and missing assignments. This problem can be circumvented by iterative construction of a "hybrid" NOE matrix comprised of experimental and calculated intensities. A problem with indirect methods is the approximate nature of the distance "measurements" which do not account properly for spin diffusion effects.

The direct approach directly incorporates NOE intensities as experimental constraints in powerful restrained dynamics simulations. This approach does not require the complete NOE matrix and provides significant improvement in accuracy due to direct accounting for spin diffusion effects. The main problem with the direct approach is that computing the gradient of the experimental potential, i.e. the gradient of each NOE intensity is very computationally intensive and needs to be done for each member of the structural family generated during the determination step, and for each time step in the restrained dynamics simulation.

Modern estimation techniques such as Kalman filters can be considered as alternative and supplementary to traditional global optimization techniques used for structural determination and refinement. The Double-Iterated Kalman Filter (hereinafter referred to as DIKF) was implemented to generate a protein structure from distances derived from NOE data, with geometrical restraints being interpreted as additional data. This approach enables both structure determination and a definitive estimate of its uncertainty and thus provides significant additional knowledge and insight on those regions of the protein which correspond to non-unique conformations.

Kalman filter techniques provide important new features for interpreting the quality of a determined molecular structure. However, since the Kalman filter is an optimal, recursive filter based on the linearization of measurement non-linearities, a significant amount of information is lost when the filter is applied to complicated, nonlinear structures such as NOE intensities. In addition, large matrix data structures are required whose straightforward manipulation severely limit the computational efficiency of these techniques when applied to large macro-molecules. Consequently, Kalman filters, including the DIKF, do not significantly improve the efficiency of determination and refinement algorithms of prior art systems, in terms of solving the multiple-minima problem.

There is a need for an improved method of determining and refining a three dimensional molecular structure, which utilizes non-linear processing techniques to solve the multiple-minima problem and which is computationally efficient.

It is therefore an object of the invention to provide an improved method of determining and refining a three dimensional molecular structure, which utilizes non-linear processing techniques to solve the multiple-minima problem in a computationally efficient manner.

Other objects and advantages of the present invention will become apparent upon consideration of the appended drawings and description thereof.

SUMMARY OF THE INVENTION

The foregoing and other objects are achieved by the invention which in one aspect comprises a computer assisted method for generating a representation of the three dimensional structure of a molecule. The representation is embodied in an n dimensional vector $X=(X_1, X_2, \ldots X_n)^T$, where n is an integer, and $X_i$ is a structural parameter, for all i from 1 to n. The set of structural parameters $X_i$ through $X_n$ may include, but is not limited to, one or more of the following classes of structural parameters, or a combination thereof: (1) three dimensional Cartesian coordinates (i.e., x, y and z) for each of the N atoms; (2) three dimensional coordinates for each of the N atoms expressed in other suitable coordinate systems, for example, internal coordinate space or dihedral angle space; (3) order parameters; (4) B-factors; and, (5) any other parameters that describe features of a molecular structure. The invention also generates a covariance matrix $P_X$ which represents the statistical uncertainty of the generated vector of structural parameters.

The user of the invention provides as input a set, or sets, of observed data for the particular molecule under consideration. This observed data may consist of, but is not limited to, one or more of the following classes, or combinations thereof: (1) experimental NMR data, including COSY (Correlated Spectroscopy) data and NOESY (Nuclear Overhauser Effect Spectroscopy) data, also known as NOE intensities; (2) experimental X-ray crystallography measurements; (3) covalent information from molecular topology/parameter data bases, e.g., bond lengths, bond angles, dihedral angles; (4) interatomic distance measurements or estimates of such distances, derived from experimental data, homology considerations, or other source; and, (5) any other class of data that is relatable to structural characteristics of the molecule. In the most general case, the observed data input to the invention is signified by $Y_{k,j}^{obs}$, with associated noise $\eta_{k,j}$. The k index corresponds to different sets of observations as a function of time, for times k=1 through K. The j index corresponds to each component of the one or more classes of observed data identified above, for all components j=1 through J. Although the number of components J may depend on the time index k, such dependency is omitted for simplicity and without loss of generality. In most applications of the invention for molecular structure determination, only one time set will be available, and hence the input observed data will be a single vector composed of components from one or more of the classes identified above, $Y_{1,j}^{obs}$ for all components j=1 through J. In cases where time sequenced measurements are available, the input observed data will be a matrix, $Y_{k,j}^{obs}$, for all k=1 to K and for all j=1 to J. In this more general case, the invention employs a propagation model to step from one time state k to the next.

The invention utilizes an analytical model g(X), which relates the observed data, Y, to the structural parameters, X. Thus, $Y^{calc}(X)=g(X)$, where $Y^{calc}(X)$ is the set of theoretical, i.e., modeled, observed data, as compared to the actual observed data $Y_{k,j}^{obs}$. The analytical model, g(X), which consists of mathematical expressions that relate each component of each class of observed data to one or more of the structural parameters $X_i$, may include, but is not limited to: (1) NMR measurements, i.e., NOE intensities, in terms of interatomic distances and the atomic coordinates; (2) X-ray crystallography measurements in terms of the atomic coordinates; (3) bond or non-bond distances between two atoms in terms of atomic coordinates; (4) bond angles and dihedral angles in terms of atomic coordinates; and, (5) mathematical relationships for any other class of observed data in terms of the appropriate structural parameters. The specific nature of the analytical model relating the observed data Y to the structural parameters X does not matter to the invention, as long as such a relationship exists and can be reduced to algorithmic form. In one aspect, for ease of use, the invention contains the analytic models for categories 1 through 4 above. In another aspect, the invention provides the means for the user to specify the analytic model algorithm relating arbitrary observed data to the corresponding structural parameters.

The user provides an initial state of the vector of structural parameters, X. The invention uses this initial state to start the nonlinear recursive filter (hereinafter referred to as NRF), which recursively processes each observed data element $Y_{k,j}^{obs}$ from the $k^{th}$ observation set, for all j=1 to J. For each observed data element $Y_{k,j}^{obs}$, the NRF recursive step consists of a prediction step, followed by an update step. Outputs of the prediction step are denoted with a ^superscript, for example $\hat{X}$, and outputs of the update step are denoted with a * superscript, for example X*, when it is necessary to distinguish between the two. During the prediction step for the $j^{th}$ element, the invention uses the vector of structural parameters, X*[k, j−1], and the associated covariance $P_X^*[k, j-1]$, from the previous $(j-1)^{th}$ element processing, and the analytic model, g(X), to compute new calculated observed data, $Y_{k,j}^{calc}(X^*[k, j-1])$, and associated covariances $\hat{P}_Y[k, j]$ and $\hat{P}_{XY}[k, j]$. The update step then computes the difference between $Y_{k,j}^{calc}(\hat{X}[k, j])$ (where $\hat{X}[k, j]=X^*[k, j-1]$ is the trivial structural parameter vector prediction step) and $Y_{k,j}^{obs}$ and uses the difference in conjunction with the covariance information $\hat{P}_Y[k, j]$ and $\hat{P}_{XY}[k, j]$ to generate a new vector of structural parameters X*[k, j], and associated covariance, $P_X^*[k, j]$. In this manner, the non-linearities contained in the analytic model are isolated in the prediction step, where they can be handled accurately and efficiently. The filtering process continues recursively for all elements of the observed data from j=1 to J, and if there are time varying observations, from k=1 to K. At the completion of the recursive filtering, the final generated vector of structural parameters, X*[K, J], represents the best estimate of the three dimensional structure of the molecule consistent with the input observed data, Y, associated uncertainties, $\eta$, and the analytic model, g(X).

The covariance-based formulation of the NRF is an important aspect of the invention. First, the covariance, $P_X^*$ provides a direct estimate of the uncertainty in the generated structural parameters. Second, it provides the memory mechanism from one recursive step to the next in the NRF. More generally, this memory mechanism enables the ability to restart, or further refine, a given molecular structure in response to new observed data without wasting the effort expended during the initial refinement.

The mathematical operations required for processing the covariance matrices in the NRF increase as the number of structural parameters for the molecule increase. One aspect of the invention, called the Refinement Wave (hereinafter referred to as RW), takes advantage of the sparse nature of the covariance matrix, and manages the NRF processing in order that the mathematical operations and required computer memory do not become prohibitive for large molecule applications. To accomplish this, the invention operates on only a small fragment, the active fragment, of the covariance matrix at any one point during NRF processing. The RW utilizes a multi-level criterion to identify and select the appropriate active fragment of the covariance matrix for processing at each step of the NRF recursion. In one embodiment of the invention, a first level criterion can exclude portions of the covariance matrix corresponding to those pairs of atoms which cannot be closer than a specified cutoff (e.g., 10 Å), given the initial structure and its a priori uncertainties. A second level criterion can identify nonessential covariances from the magnitudes of correlations evidenced in the mutual covariance $P_{XY}$, and excludes all low magnitude elements from subsequent mathematical operations. Additional levels in the criterion can manage active/passive memory exchanges.

These aspects of the RW element of the invention enable an important asymptotic property, in that the computational time scales as n, where n is the number of structural parameters, as opposed to $n^2$ or greater for most prior art methods. In addition, since the RW only requires a relatively small portion of the covariance matrix in active memory at one point during the processing, the invention can be applied, in principle, to a molecule of any size using only moderate computer memory and speed resources.

BRIEF DESCRIPTION OF DRAWINGS

The foregoing and other objects of this invention, the various features thereof, as well as the invention itself, may be more fully understood from the following description, when read together with the accompanying drawings in which.

DETAILED DESCRIPTION OF THE INVENTION

Figure 1:
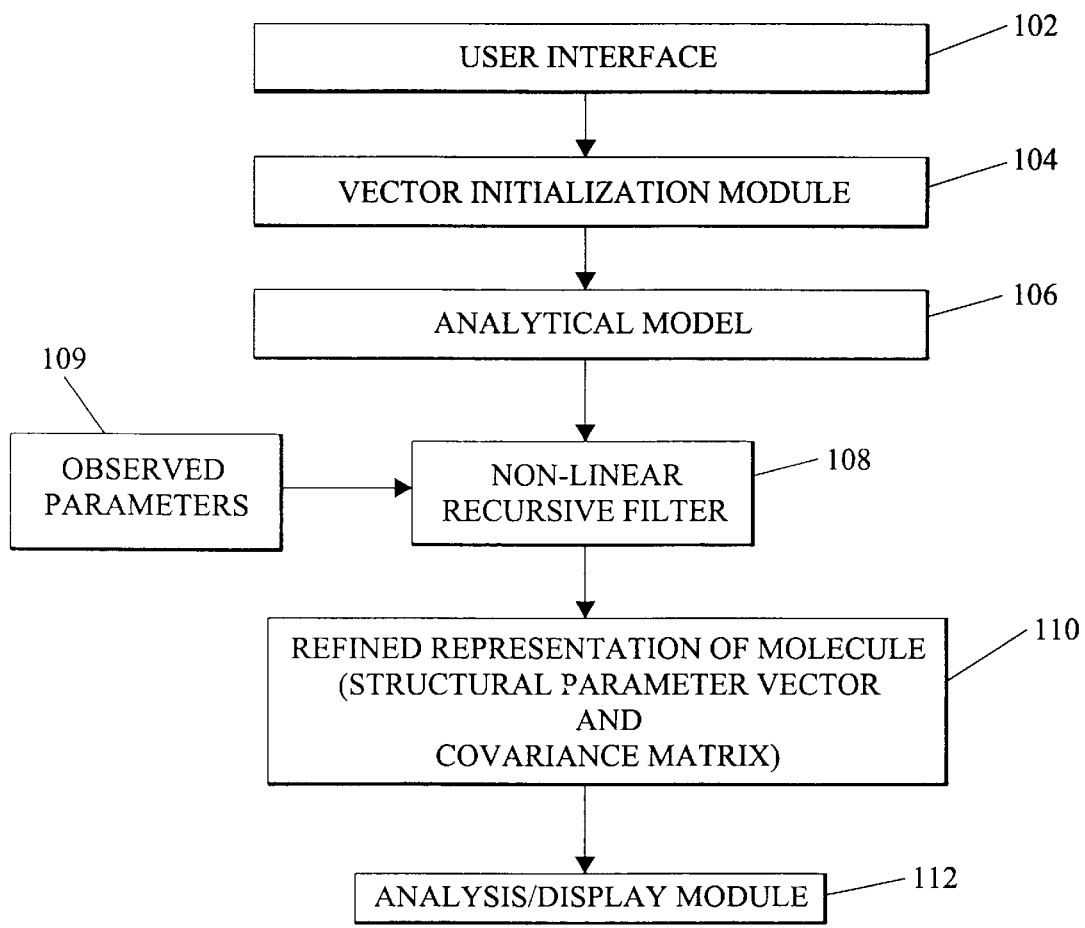
FIG. 1 shows exemplary steps of a computer-implemented method of generating a representation of the three dimensional structure of a molecule.

The present invention is a computer system for generating a representation of the three dimensional structure of a molecule. An embodiment of the invention is shown in FIG. 1. In that figure, a user operates a programmed digital computer 100 which initiates and controls operation of the invention, via user interface 102. The invention also includes a vector initialization module 104 which establishes and initializes the vector of structural parameters, an analytical model 106, a non-linear recursive filter 108 which receives a set of observed parameters 109 and the vector of structural parameters to produce a refined representation of a molecule 110, and an analysis and display module 112 to analyze and display the refined representation of the three dimensional structure of a molecule.

Figure 2:
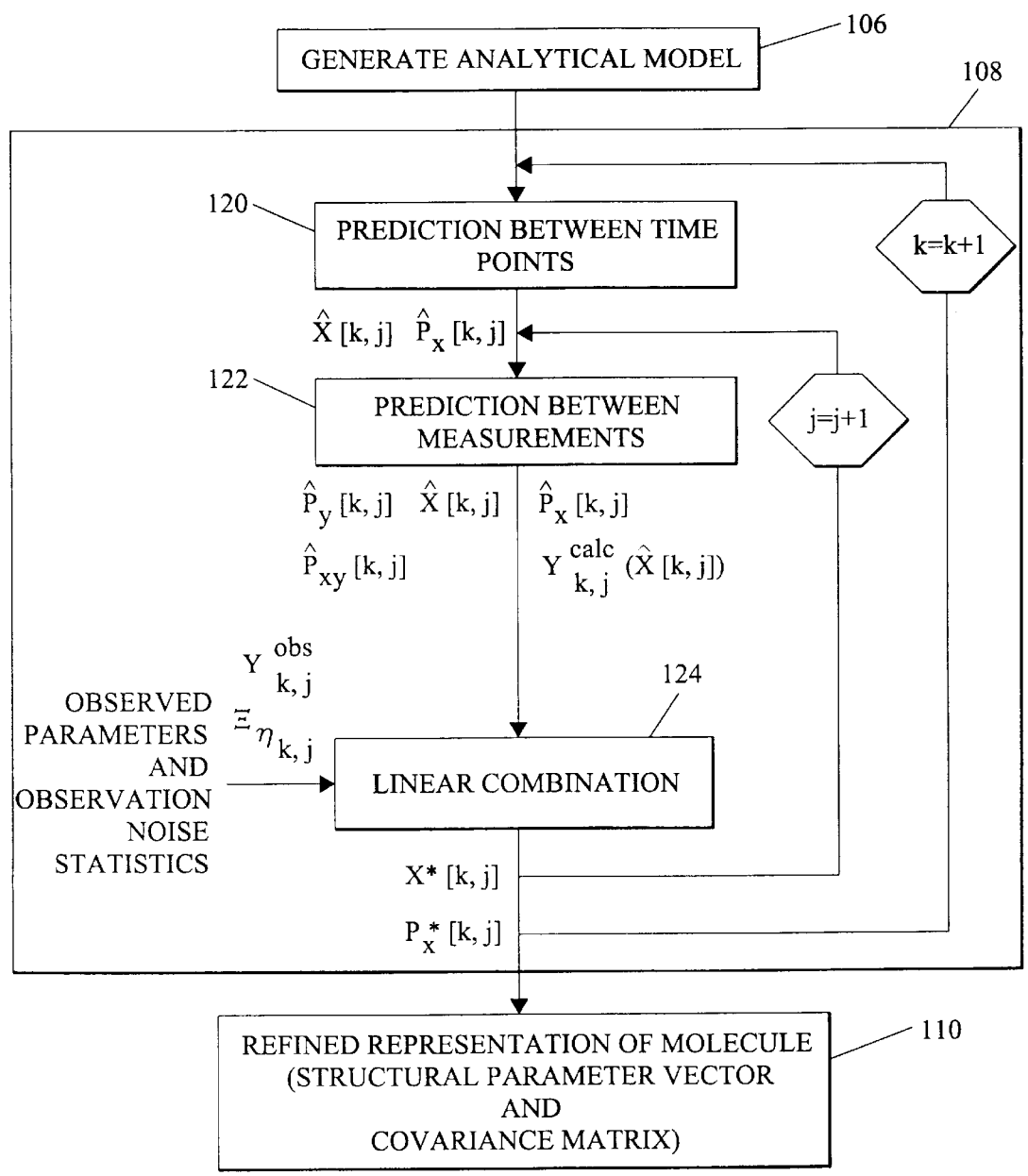
FIG. 2 shows exemplary substeps of non-linear recursive filtering step of FIG. 1.

The detailed substeps necessary to implement the non-linear recursive filter 108 are shown in FIG. 2. As described more completely below, the prediction between-time-points substep 120 receives the most recent vector of structural parameters, either the initial vector or the vector generated from the previous iteration of the recursive filter and its corresponding covariance matrix, and models the time evolution of the vector of structural parameters. The prediction-between-measurements substep 122 receives the time-evolved vector of structural parameters and its corresponding covariance matrix, and produces a prediction, $\hat{X}[k, j]$, of the next state of the vector of structural parameters and its corresponding covariance matrix, $\hat{P}_X[k, j]$, a prediction, $Y_{k,j}^{calc}(\hat{X}[k,j])$, of the next state of the analytical model, and the corresponding covariance matrix $\hat{P}_Y[k, j]$, and a covariance matrix $\hat{P}_{XY}[k, j]$ corresponding to a correlation of $\hat{X}[k, j]$ and $Y_{k,j}^{calc}$. The linear combination substep 124 receives the output of the prediction-between-measurements substep 122 along with observed parameters $Y_{k,j}^{obs}$ and the statistical variance $\Xi_{\eta k,j}$ of the observation noise $\eta$ for the $j^{th}$ observed parameter at time instant k, and generates a new state of the vector of structural parameters $X^*[k, j]$ and the corresponding covariance matrix $P_X^*[k, j]$, based upon a linear combination of the inputs.

The objective of one embodiment of the invention is to generate $X^*$, an optimal estimate of the vector of structural parameters X, which matches the observed parameters $Y^{obs}$ in the best way, given conditions such as the analytical model of $Y^{obs}$, $Y^{calc}$, and the observation noise, $\eta$. In other embodiments of the invention, the optimal estimate of the vector of structural parameters may also depend upon an analytical model of the time evolution of the vector X. The vector of structural parameters X includes a set of structural parameters $X_i$, for all i from one to n, where n is an integer. Each of the structural parameters $X_i$ contributes to defining the three dimensional structure of the molecule. In one form of the invention, the structural parameters $X_i$ represent the Cartesian coordinates of the constituent atoms of the molecule. Each of the observed parameters $Y_{k,j}^{obs}$ (where $Y_{k,j}^{obs}$ represents the $j^{th}$ parameter observed at time k) can be expressed as a function of the structural parameters of two or more atoms, thus forming a model, $Y^{calc}(X)=g(X)$. For example, in the form of the invention for which the vector of structural parameters X represents the Cartesian coordinates of all of the atoms of the molecule, a particular observed parameter $Y_{k,j}^{obs}$ may be the distance between two atoms, measured using any one of several existing techniques. If the Cartesian coordinates $(x_1, y_1, z_1)$ of a first atom are represented by the components $X_1$, $X_2$ and $X_3$ of the vector X, respectively, and the Cartesian coordinates $(x_2, y_2, z_2)$ of a second atom are represented by the components $X_4$, $X_5$ and $X_6$ of the vector X, respectively, then the calculated distance between the atoms expressed as a non-linear function of the elements of X (i.e., $Y^{calc}(X)=g(X)$) is:

$$\text{distance} = Y^{calc} = \sqrt{(X_4 - X_1)^2 + (X_5 - X_2)^2 + (X_6 - X_3)^2} \quad (1)$$

In this example, the invention generates an optimal set of elements $X_1$, $X_2$, $X_3$, $X_4$, $X_5$ and $X_6$, which minimizes the difference between the measured distance and the calculated distance.

There are many established approaches to resolving such an optimization problem. A standard approach is to seek to minimize a cost function J(X) with respect to X:

$$J(X) = \sum_{i=1}^{L_{exp}} w_i^{exp}(Y_i^{obs} - Y_i^{calc}(X))^2 + \sum_{i=1}^{L_{chem}} w_i^{chem} h_i(X) \qquad (2)$$

where h(X) represents a priori knowledge of chemical information regarding the molecule, interpreted as constraints, restraints, or energy terms to be minimized, and the variables wi are weighting coefficients that convolve a set of experimental and chemical data into a scalar cost function.

The challenges of the problem as formulated reside in the high dimensionality of atomistic models and in the highly non-linear nature of the functions forming the models. In large macro-molecules, the number of elements in the vector X can reach tens of thousands and more. These challenges not only impede the implementation of regular optimization methods, but they usually make them ineffective. For example, well-known optimization techniques, like the conjugate gradient method or the Powell downhill method, provide only local solutions, since the refinement process terminates in the nearest local minimum. To allow for a broader exploration of the conformational space in Nuclear Magnetic Resonance (hereinafter referred to as NMR) refinement, molecular dynamics with chemical h(X) and experimental $\|Y^{obs} - Y^{calc}(X)\|$ potentials provides a physically meaningful search trajectory that also asymptotically minimizes J(X). Simulated Annealing (hereinafter referred to as SA) is a standard method used to escape local minima by using high temperatures and slow cooling schedules. (see Clore, G. M., et al., *Journal of Molecular Biology*, 1986. 191: p. 523, and Nilges, M., G. M. Clore, and A. M. Gronenborn, *FEBS Letters*, 1988. 229: p. 317.)

Recursive filtering offers a conceptually different way of finding the global minimum, i.e., the optimal vector X*. The cost function J(X) is not a general function of n variables; it is the result of convolving a large amount of geometrical and experimental data into a scalar. This convolution produces a complex multiple local minima function, while the model for each individual term is usually a simple non-linear function with advantageous analytical properties (e.g. convexity). For example, bond lengths (as shown in the example above) and Nuclear Overhauser Effect (hereinafter referred to as NOE) distances are modeled by non-linear functions of coordinates attributed to two atoms. Also, NOE intensities are functions of the inter-proton distances within a spherical cutoff of 4 Å around the interacting proton pair. The foregoing information suggests that processing each elementary function separately will lead to a simpler, more efficient solution. Recursive filtering enables a search trajectory in the "informational space", i.e. for a given time k, for each observation $Y_{k,j}^{obs}$, for all j from 1 to J, where J is an integer representing the total number of observation parameters gathered at time k. This entails a recursive update of the structure after processing each observation such as experimental measurements, geometric constraints, and van der Waals forces.

The theoretical roots of recursive filtering are in the Kalman filter approach, which originated with Kalman and others in the 1960's. (see Kalman, R. D., *Journal of Basic Engineering* (ASME), 1960. 82D: p. 35, and Jazwinsky, A. H., *Stochastic Processes and Filtering Theory*. 1970, New York: Academic Press.) The Kalman filter is an optimal, recursive filter for linear systems with Gaussian uncertainties. The Kalman filter recursively improves a set of parameters compatible with measurement data, given the observation model and statistical characteristics of the measurement noise. The set of structural parameters is characterized by a multi-dimensional Gaussian distribution (i.e., a Gaussian hyper-ellipsoid) where the vector of mathematical expectations defines the average structure and the covariance matrix characterizes associated uncertainties and defines an ensemble of structures. In linear filtering problems there is no multiple local minima problem, so the Kalman filter will provide the optimal estimate of X and the measure of its quality. But in non-linear problems, such as NMR structure determination and refinement, this procedure will be divergent in general.

The Extended Kalman Filter (hereinafter referred to as EKF) was developed to avoid divergence in non-linear applications. EKF performs adaptive linearization of non-linearities in the vicinity of the current estimate. More sophisticated versions of the EKF, such as the Double-Iterated Kalman filter (hereinafter referred to as DIKF) entail re-iteration in computing the sensitivity matrices for each single observation and re-starting the entire filtering process from the refined estimates and initial a priori uncertainties. The application of the DIKF for structure determination and refinement (see Pachter, R., R. B. Altman, and O. Jardetzky, *Journal of Magnetic Resonance*, 1990. 90; Pachter, R., R. B. Altman, and O. Jardetzky, *Journal of Magnetic Resonance*, 1990. 89; Koehl, P., J. F. Lefevre, and O. Jardetzky, *Journal of Molecular Biology*, 1992. 223: p. 299–315; Delfini, D., C. Nicolini, and E. A. Carrara, *Journal of Computational Chemistry*, 1996. 17: p. 74–86.) as well as applications in the aerospace field indicate that linear or linearized recursion may result in incorrect changes to the estimates in the case when the refinement problem acquires significant multiple local minima structure, due to the non-linearity of the measurements. In this case, global optimization might be a better solution. Indeed, studies (see Delfini, D., C. Nicolini, and E. A. Carrara, *Journal of Computational Chemistry*, 1996. 17: p. 74–86.) demonstrate that a parallel version of the DIKF, which processes all measurements at once, i.e., global least-squares optimization, performs better in some problems than sequential DIKF, which processes measurements recursively. In order to make the best use of recursion, it is necessary to retain as much as possible the non-linear character of the observations at each step.

The non-linear recursive filtering approach consists of extending the vector of parameters X at each $k^{th}$ time moment and at each jth measurement during recursive filtering, i.e., $$X \to X_\Sigma = \begin{pmatrix} X \\ Y_{k,j}^{calc} \end{pmatrix} \text{ where } Y_{k,j}^{calc} = g_{k,j}(X) \qquad (3)$$

This forms the linear observation model:

$$Y_{k,j}^{obs} = (0_{1 \times n} \vdots 1) \begin{pmatrix} X \\ Y_{k,j}^{calc} \end{pmatrix} + \eta_{k,j} \qquad (4)$$

The non-linear recursive filter (hereinafter referred to as NRF) includes a prediction step and an update step at each single observation. These steps are realized recursively to process each single observation. Gaussian, zero mean observation noise $\eta_{k,j}$, with variance $\Xi_{\eta k, j}$, gives the problem a statistical nature. At the prediction step, between two measurements signified by indices j−1 and j and observed at time instant k, the NRF treats observation non-linearities through statistical analysis, for each block of the vector $X_\Sigma$, as defined by the following five equations:

$$\hat{X}[k,j] = X^*[k,j-1]; \quad (5)$$

$$\hat{P}_X[k,j] = P_X^*[k,j-1]; \quad (6)$$

$$Y_{k,j}^{calc}(X[k,j]) = E[g_{k,j}(X[k,j])]; \quad (7)$$

$$\hat{P}_Y[k,j] = \text{Cov }[g_{k,j}(X[k,j])]; \text{ and,} \quad (8)$$

$$\hat{P}_{XY}[k,j] = \text{Cov}[X[k,j] \cdot g_{k,j}(X[k,j])]. \quad (9)$$

The notation $\hat{X}[k, j]$ represents a prediction of the estimate of the vector X at time instant k, given measurements up to the index j−1, i.e., a prediction of the estimate of the vector X at the instant the measurement j is taken, but before the information from measurement j is processed. Equation (5) indicates that the prediction of the next state of the vector X is simply the previous state of X. Equation (6) indicates that the prediction of the covariance matrix associated with the predicted vector $\hat{X}[k, j]$ is the same as the covariance matrix associated with the vector $X^*[k, j−1]$, which follows from the fact that $\hat{X}[k, j]$ equals $X^*[k, j−1]$, as asserted in equation (5). Equation (7) indicates that the prediction of the next state of the analytical model $Y_{k,j}^{calc} = g(\hat{X}_{k,j})$ is the statistical expected value, expressed by the notation E[], of the analytical model operating on the vector X, assuming the statistical characteristics of the vector X up to the moment when the (j−1)$^{th}$ measurement was processed. Equation (8) indicates that the prediction of the next state of the variance associated with the analytical model is the mathematical covariance matrix operation, expressed by the notation Cov [], performed on the analytical model operating on the vector X, assuming the statistical characteristics of the vector X up to the moment when the (j−1)$^{th}$ measurement was processed. Equation (9) defines a covariance matrix relating to product terms of the vector X and the analytical model, assuming the statistical characteristics of the vector X up to the moment when the (j−1)$^{th}$ measurement was processed. The three covariance matrices $P_X$, $P_Y$ and $P_{XY}$ are the corresponding blocks (X, Y and XY) of the covariance matrix for the extended vector $X_\Sigma$.

At the update step, the NRF refines the prediction of X by the j$^{th}$ observation at the k$^{th}$ time moment:

$$X^*[k,j] = \hat{X}[k,j] + \left(\frac{\hat{P}_{XY}[k,j]}{Y[k,j]}\right) \cdot \left(Y_{k,j}^{obs} - Y_{k,j}^{calc}(\hat{X}[k,j])\right); \quad (10)$$

$$P_X^*[k,j] = \hat{P}_X[k,j] - \left(\frac{1}{Y[k,j]}\right)\hat{P}_{XY}[k,j] \cdot \hat{P}_{XY}^T[k,j]; \text{ and,} \quad (11)$$

$$Y(k,j) = \Xi_{\eta_{k,j}} + \hat{P}_Y[k,j]. \quad (12)$$

The NRF has additional equations in the general case when the measurements are collected at different time moments k, where k=1, 2, . . . , K , and the state vector X evolves between the k$^{th}$ and (k+1)$^{th}$ moments according to the non-linear dynamical stochastic equation:

$$X[k+1] = f_k(X[k], \zeta[k]), \quad (13)$$

where $f_k( )$ is an n-dimensional vector-function, and $\zeta$ is an m-dimensional Gaussian random vector with the zero mean and an associated covariance matrix $\Xi_\zeta$ which formalizes the statistical character of the molecular motion. Note that in general, the vector-function $f_k( )$ can be time-varying, as indicated by the subscript k. For simplicity, and without loss of generality, the subscript k is hereinafter omitted. The prediction equations between the time moments k and k+1 are defined similarly to the prediction equations (7) and (8):

$$\hat{X}[k+1, 1] = E[f(X[k, J])]; \quad (14)$$

$$\hat{P}[k+1, 1] = \text{Cov}[f(X[k,J])]. \quad (15)$$

Equation (14) indicates that the prediction for the evolution of the state vector X to the next time moment is the statistical expected value of the analytical model f( ) operating on the vector X. Equation (15) indicates that the prediction of the next state of the covariance matrix associated with the analytical model f( ) is the mathematical covariance matrix operation performed on the analytical model f( ) operating on the vector X. Note that both in equation (14) and in equation (15), the statistical characteristics of the vector X correspond to the moment when all J measurements at the k$^{th}$ time instant were processed (this is signified by the notation [k, J]). Also, the notation [k+1, 1] symbolizes the fact that the predicted state vector at the time k+1 corresponds to the event before processing the first measurement of the data set at time k+1.

Equations (5) through (15) comprise the NRF. Equations (5) through (9) comprise the prediction portion of the NRF between two measurements, while equations (10) through (12) comprise the update portion of the NRF. In the general case of a dynamic time evolution model for the vector X defined by equation (13), the prediction portion of the NRF also includes equations (14) and (15) to propagate the state vector X between two time instants. With k=1 and j =1, the initial conditions are provided for the NRF as:

$$\hat{X}[1, 1] = X_o$$

and $$\hat{P} = P_o,$$

where $X_o$ and $P_o$ describe the initial (a priori) structure and its uncertainty, respectively. In one form of the invention, $X_o$ is produced from a topology database, although those skilled in the art will recognize that an initial state vector may be produced from parameter databases, molecular primary structure databases, distance geometry calculations, simulated annealing calculations, restricted molecular dynamics calculations, amino acid sequence/primary structure databases, amino acid helical location data, and combinations thereof.

The NRF as described by equations (5) through (15) is optimal, in the class of Gaussian approximations, and simple, compared with prior art non-linear filters in the space of X. The invention's effectiveness and efficiency derives from the fact that the non-linearities are isolated in the prediction step where the expectation and covariance operations and can be performed analytically due to the relatively simple non-linear structure of the physical measurements considered.

The vector-matrix structure of the NRF is explicitly defined by equations (10), (11), and (12), and only the physical measurement functions $g_{k,j}(X)$ need to be specified in order to perform the statistical operations of the first four NRF equations. One form of the invention is based on an atomistic model in which the positions of the N atoms comprising the molecule are defined by an n-dimensional vector, where n=3N, of Cartesian coordinates. The model $g_{k,j}(X)$ for each bond between two atoms, bond angle, and dihedral angle is a simple non-linear function attributed, correspondingly, to 2, 3, and 4 atoms. By contrast, the model $g_{k,j}(X)$ corresponding to each NOE intensity observation is considerably more complex, especially when spin diffusion effects are taken into account.

The invention uses the standard formalism for calculating the volume of an NOE intensity cross-peak between spins i and j, $I_{ij}^c$, from the atomic coordinates by means of the relaxation matrix R:

$$I_{i,j}{}^c \alpha [\exp(-R\pi_m)]_{i,j}, \qquad (16)$$

where $\pi_m$ is the mixing time. The dependence of the relaxation matrix R on the distances between protons is described in several sources. (see Yip, P. and D. Case, *Journal of Magnetic Resonance*, 1989. 83: p. 643, Yip, P. and D. Case, *Computational Aspects of the Study of Biological Macromolecules by NMR Spectroscopy*. 1991, New York: Plenum Press, and Brunger, A. T., X-PLOR (vers 3.1), *A System for X-ray Crystallography and NMR*. 1992, New Haven and London: Yale University Press.)

According to accepted practice in the art, the invention uses a distance cutoff of 4.5 Å and performs relaxation matrix calculations for each pair of spins i and j, where i and j are arbitrary indexing integers.

The non-linear nature of the NRF is stipulated by the degree of non-linearity kept in the statistical operations. If second and third order Taylor approximations are used to describe the non-linearities of the model $Y_{k,j}{}^{calc}$, the calculations represented by equations (5), (6), (7), (8), and (9) are reduced to simply computing the second-order statistics of quadratic and cubic functions with a Gaussian argument. For geometrical measurements and van der Waals forces, these calculations are very simple due to the dependence of each component of the model $Y_{k,j}{}^{calc} = g_{k,j}(X)$ on only a very limited number of structural parameters.

In the case of NOEs, however, the number of spins contributing to the diffusion effect can reach a few dozen for long mixing times. In this case the realization of the matrix exponential of equation (16), its derivatives, and the statistics of equations (10), (11) and (12) pose computational problems. The invention utilizes an efficient procedure to mitigate these difficulties. First, the invention computes second order derivatives of each NOE observation with respect to Cartesian coordinates using the generalized formula of Yip and Case (see Yip, P. and D. Case, *Computational Aspects of the Study of Biological Macromolecules by NMR Spectroscopy*. 1991, New York: Plenum Press.). Next, the invention selects only the essential derivatives for the statistical analysis of equations (10), (11) and (12). Following common prior art practice for the refinement of structures with large initial uncertainties, the invention uses a two-spin approximation of each NOE for the first few cycles of the NRF.

From a physical standpoint, the NRF offers a conceptually new method for sampling the conformational space by the gradual exclusion of those conformations that are improbable due to the covalent geometry and experimental data. Mathematically, this means that the refinement process in n-dimensional conformational space is viewed not as a process of searching for a single global minimum representing the true structure, but as the process of recursive transformation of a large a priori n-dimensional, statistical ellipsoid into a small a posteriori ellipsoid or set of ellipsoids, representing a statistical set of structures. Recursion helps alleviate the multiple-local-minima problem by gradually narrowing the search area around the global minimum and, thus, preventing the NRF from looking for a solution among already improbable local minima. The highly non-linear nature of the NRF significantly reduces the probability of excluding the global minimum itself from further search, an error that is quite possible with prior art methods such as the DIKF.

The performance advantage of the NRF derives from the fact that the non-linear recursion requires, in principle, only one vector function evaluation. The non-linear function for each measurement is computed only once, which is equivalent to one function evaluation of the cost function of equation (2). This is especially important for cases where the prediction of the measurement is computationally expensive, like in the case of direct refinement from NOE intensities. In practice, however, the NRF may require a few additional recursions, since it still remains a Gaussian approximation of the a posteriori density of probabilities, i.e., $p(X \sqcup Y)$. Seven to ten cycles are usually sufficient to start structure determination and refinement from a nearly random initial vector $X_o$, whereas one recursion normally suffices for initial uncertainties of 2-3 Å. By contrast, the SA method normally requires thousands of function evaluations. The performance advantage of the invention is mainly attributed to the covariance matrix corresponding to the vector of structural parameters. The importance of the covariance matrix is two-fold. First, the covariance matrix provides the memory mechanism necessary for a recursive filter, which in turn overcomes the multiple-minima problem. Second, the covariance matrix provides a measure of refinement quality in terms of uncertainty ellipsoids representing a statistical set of candidate structures. In other words, the information on correlation links between structural parameters enables local-minima-escape trajectories, and provides a tool for assessing the accuracy of the resulting structures.

In other forms of the invention, the recursive processing described herein may be replaced or supplemented by batch processing, wherein two or more physical observations may be processed simultaneously. Batch processing may include tradeoffs with respect to computational efficiency, but can provide similar computational results. For some sets of physical observations, batch processing may provide advantages over recursive processing.

Figure 3:
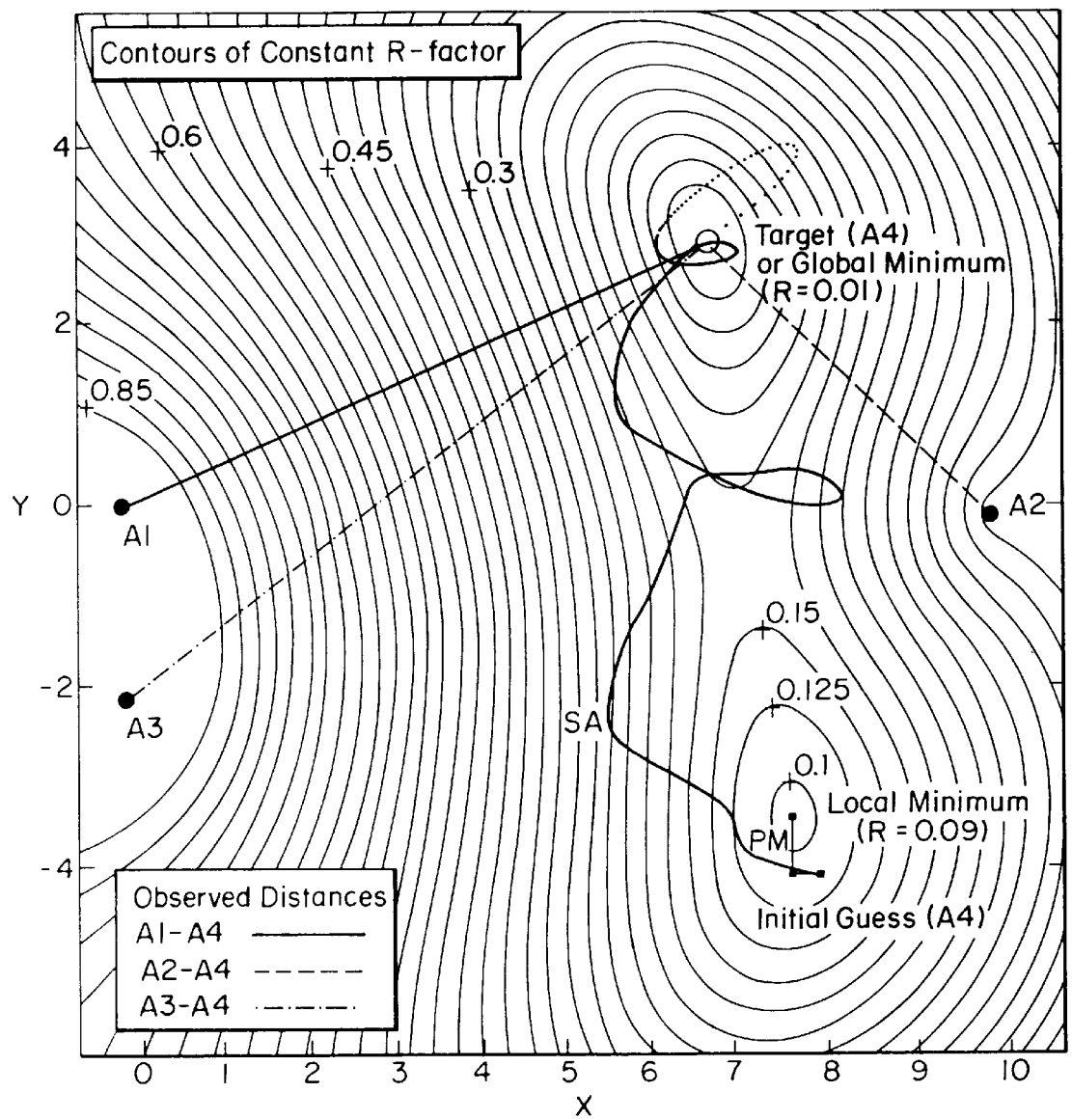
FIG. 3. shows a four atom, two dimensional example of the prior art resolution of a multiple local minima problem.
Figure 4:
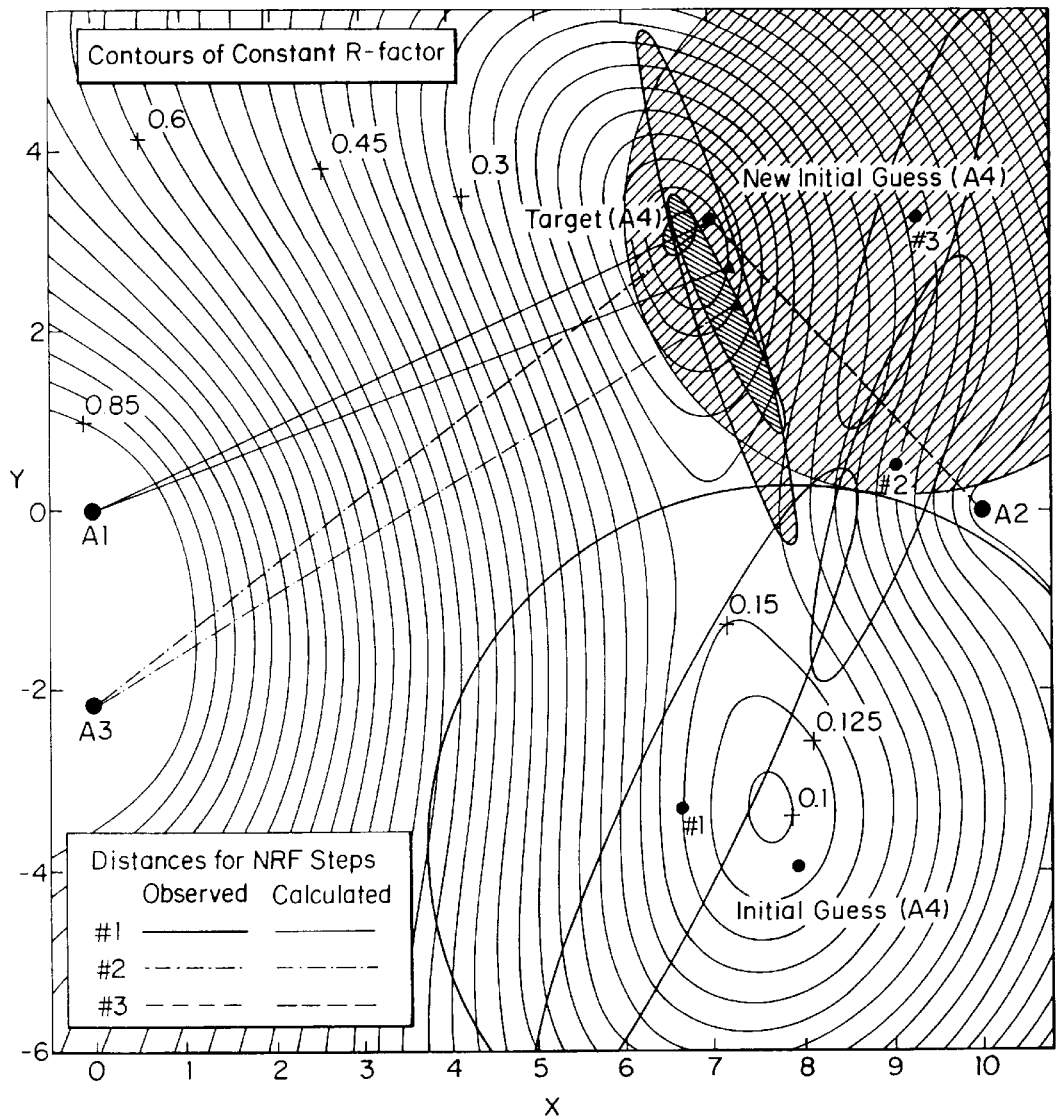
FIG. 4 shows a four atom, two dimensional example of the invention resolution of a multiple local minima problem.

The simple, two dimensional example shown in FIG. 3 and FIG. 4 illustrates the concepts embodied in the invention. In FIG. 3, the two dimensional Cartesian coordinates of the atoms labeled A1, A2 and A3 are known while the corresponding coordinates of atom A4 are to be estimated from the three observed distances $d_{1 \to 4}$, $d_{2 \to 4}$ and $d_{3 \to 4}$, where $d_{x \to y}$ represents the distance from atom x to atom y. The cost function of equation (2), written as the difference between observed and calculated distances, has two minima. Contours of constant normalized cost function, known as R factors to those skilled in the art, are shown on FIG. 3 and FIG. 4. The initial guess for atom A4 is given quite close to the local minimum, but far away from the global minimum. FIG. 3 demonstrates that the Powell downhill method quickly terminates in the local minimum, improving the R-factor from 0.12 to 0.09. Simulated annealing, which may be modeled as the motion of a heavy ball, coupled to fluctuating (heat bath) and dissipating (heat sink) energy terms (for information on Langevin dynamics see Allen, M. P. and D. J. Tildesley, *Computer Simulations of Liquids*. 1987, Oxford: Clarendon Press), is capable of escaping the local minimum and finds the global minimum after a sufficiently long simulation, for example, 200 integration steps. FIG. 4 demonstrates that the NRF finds the global minimum after two cycles. In the example of FIG. 4, the Gaussian ellipsoids for the second cycle are shadowed. The NRF is initiated with an a priori ellipsoid that does not contain the global minimum. After processing the distance $d_{1 \to 4}$, the NRF evaluates an elongated ellipsoid which is turned toward the global minimum. After processing the distance $d_{3 \to 4}$, and then distance $d_{2 \to 4}$, the NRF securely excludes the local minimum from further search. The second cycle starts from a smaller a priori ellipsoid. The NRF again processes the distances in the sequence $d_{1\to4}$, $d_{3\to4}$, and $d_{2\to4}$, and evaluates three new ellipsoids. The last and smallest ellipsoid contains the true position of the atom A4, while the shape and size of the ellipsoid provide a statistical measure of the accuracy of the estimate that accounts for noise in observing the distances. The efficiency advantage provided by the invention is demonstrated by the fact that the NRF requires only two evaluations of the cost function J(X) and its derivatives to isolate the global minimum, while SA requires 200 such evaluations. In this example, the initial ellipsoid chosen did not contain the true position of the atom A4. Such a choice is likely to occur if the structural information used to produce the initial structural vector lacked accuracy. However, if the initial ellipsoid had included the true position of A4, in most cases only one cycle of the NRF would have been necessary in FIG. 4. Consequently, the performance of the invention is improved as the initial vector $X_o$ is made more accurate.

The NRF performs mathematical operations on a covariance matrix of size n×n, representative of a n-dimensional hyper-ellipsoid. For large macromolecules, the number of structural parameters, n, may be so large that conventional software routines for implementing such mathematical operations cannot practically be used. The invention uses a technique called a refinement wave (hereinafter referred to as RW) to process such large molecules. The following example, shown in FIG. 5 and FIG. 6, illustrates the RW principle on a hexapeptide (ARG-PRO-ASP-PHE-CYX-LEU) with 250 synthetic NOE intensities.

Figure 5:
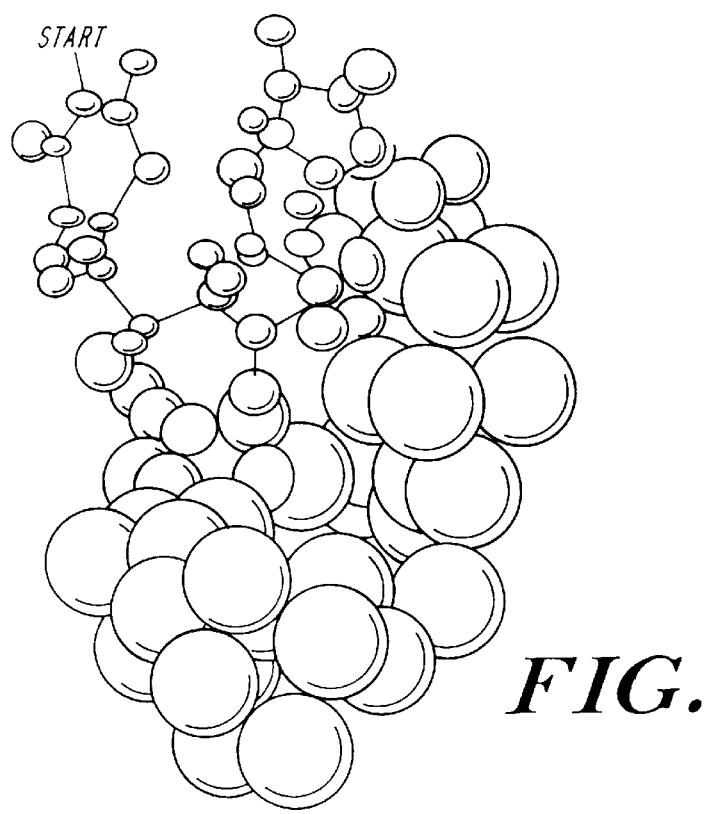
FIG. 5 shows a representation of the three dimensional structure of a molecule partially through the refinement wave processing.
Figure 6:
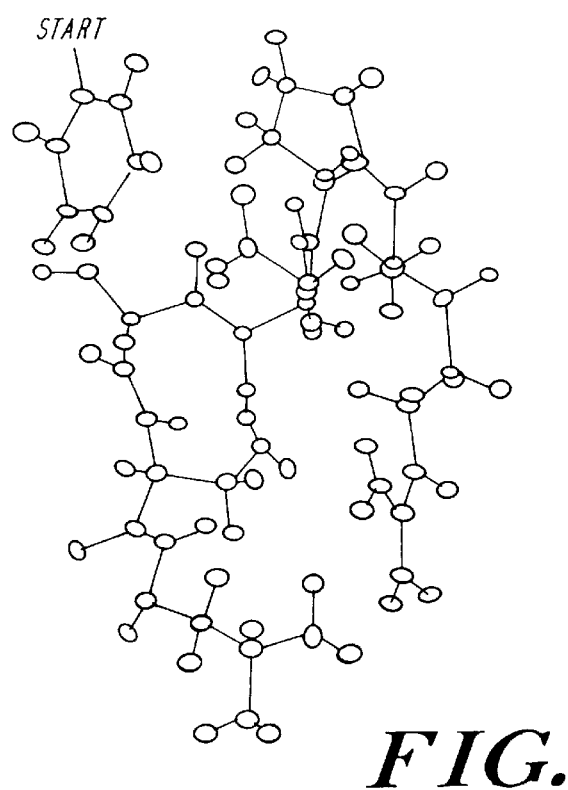
FIG. 6 shows a representation of the three dimensional structure of a molecule completely through the refinement wave processing.

The RW starts at the upper left-hand corner of the molecule as it is viewed in FIG. 5, and proceeds "downward" to process new observed parameters and geometrical restraints. FIG. 5 represents an intermediate stage in the RW technique when only part of the data has been processed. The upper part of the hexapeptide is already refined, and further processing of all remaining NOE intensities, the result of which is shown in FIG. 6, does not provide further improvement to the portion of the molecule already refined at the intermediate stage shown in FIG. 5. The ellipsoids shown in FIG. 5 and FIG. 6 represent a set of structures compatible with the noisy data. The structure representing the true positions of the atoms falls within the space defined by the ellipsoids.

The mechanism of the RW is based on recursive improvement and transmission of measurement information through the uncertainty ellipsoids. In terms of the covariance matrix operations, this means that during the processing of each single observation, the invention operates on only a small fragment of the covariance matrix. One embodiment of the invention employs a two level criterion to identify and select the active fragments of the covariance matrix, although those skilled in the art will recognize that other embodiments of the invention may incorporate multiple level criteria.

In the two level criterion embodiment of the invention, the first level of the criterion excludes portions of the covariance matrix corresponding to those pairs of atoms which cannot be closer than 10 Å, given the initial structure and its a priori uncertainties. The second level of the criterion is statistical and is based on analysis of the mutual covariance vector $P_{XY}$ which establishes correlations between the vector of structural parameters X and the current observation model component $Y^{calc}$. Evaluation of $P_{XY}$ according to the NRF equations (10), (11), and (12) is a simple vector operation. The main computational difficulty lies in performing the outside vector product $P_{XY}P_{XY}^T$ which requires approximately $n^2$ multiplications. The invention drastically reduces the computational requirements of this outside vector product by excluding all non-essential covariances and exploiting the resulting sparse nature of the covariance matrix. The invention identifies the non-essential covariances by computing the correlation coefficients for the covariance components of the vector $P_{XY}$, sorting the correlation coefficients in three groups labeled 1) high correlation, 2) medium correlation and 3) low correlation, and then excluding multiplications for small/small and small/medium pairs.

Since RW involves only a region of the molecule roughly 5 Å to 10 Å in radius during any on-going refinement, the invention excludes from the active memory information relating to regions not effected by the RW. Consequently, the invention can handle molecules of any size, in principle, using only moderate memory and speed resources. The RW element of the invention has an important asymptotic property: the RW computation cost scales as n, where n is the number of structural parameters. If the cost of one step of the RW is S, limited by the active region, and new $N_{rate}$ atoms are covered by the wave, then the cost of refining the entire molecule is $S \cdot (n/3N_{rate})$.

The present embodiments are therefore to be considered in all respects as illustrative and not restrictive, the scope of the invention being indicated by the appended claims rather than by the foregoing description, and all changes which come within the meaning and band of equivalency of the claims are therefore intended to be embraced therein.

What is claimed is:

1. A computer-assisted method for generating a representation of the three dimensional structure of a molecule, said representation being an n-dimensional vector of structural parameters $X[q, r] = (X_1[q, r], X_2[q, r], \ldots X_n[q, r])^T$, at an associated pair of index integers q and r, n being an integer, $X_i[q, r]$ being a structural parameter, said $X[q, r]$ having a statistical uncertainty, and a covariance matrix $P_X[q, r]$ representative of said statistical uncertainty of said vector of structural parameters, comprising the steps of:

A. providing m sets of observed data, m being an integer, each of said sets of observed data including a plurality of observed data elements, each of said observed data elements being relatable to at least one of said structural parameters and having an associated observation noise;

B. providing a first analytical model $g_{q, r}(X[q, r])$, where $g_{q, r}(X[q, r])$ defines one or more mathematical expressions representative of the relationship of each observed data element to one or more of said structural parameters $X_i[q, r]$, and $g_{q, r}(X[q, r])$ is representative of an analytical vector $Y_{q, r}^{calc}(X[q, r])$;

C. generating an updated estimate of said structural parameters having an updated statistical uncertainty, and generating a corresponding updated covariance, representative of said updated statistical uncertainty of said updated structural parameters, by filtering said observed data elements with a non-linear recursive filter utilizing said first analytical model $g_{q, r}(X[q, r])$, said updated estimate of said structural parameters being representative of the three dimensional structure of said molecule.

2. A method according to claim 1, wherein said step of generating an updated estimate of said structural parameters includes a non-linear recursive filter sequentially processing each of said observed data elements.

3. A method according to claim 1, wherein said step of generating an updated estimate of said structural parameters includes a non-linear batch filter simultaneously processing said data elements as a group.

4. A method according to claim 1, wherein said step of generating an updated estimate of said structural parameters further includes the substeps of:

i. providing one of said observed data elements,
  ii. generating a predicted vector from an updated vector of a next previous recursion step;
  iii. generating said analytical vector from said predicted vector and generating covariances associated with said analytical vector and said predicted vector;
  iv. evaluating a difference between said observed data element and at least one element of said analytical vector, and generating an updated vector of structural parameters and associated updated covariance as a function of said difference and said associated covariances.

5. A method according to claim 4, wherein said method further includes the step of excluding a plurality of elements of said covariances, prior to said difference evaluating substep, including the following substeps:

i. excluding a plurality of elements of said covariance matrix $P_X[q, r]$, said plurality of elements being representative of pairs of atoms having a center-to-center spacing of at least d, d being a predetermined distance;
  ii. generating a correlation coefficient for each component of a matrix $P_{XY}[q, r]$, each component of said matrix $P_{XY}[q, r]$ corresponding to a cross term between said analytical vector and said predicted vector;
  iii. sorting said correlation coefficients into a plurality of categories, said categories being representative of a correlation range; and,
  iv. excluding at least one pairing of said categories from subsequent matrix operations with $P_{XY}[q, r]$ matrix.

6. A method according to claim 5, wherein said predetermined distance d is 10 Å, and said plurality of categories defines a high correlation category, a medium correlation category and a low correlation category, and said excluding substep excludes low/low category pairings and low/medium category pairings.

7. A method according to claim 4, wherein said mathematical expressions of said first analytical model include non-linear expressions to generate said predicted vector, whereby said non-linear expressions are isolated from said updated vector generating substep and said updated covariance generating substep.

8. A method according to claim 4, wherein said function in substep (iv) is linear.

9. A method according to claim 1, wherein said method further includes the step of providing an initial estimate of said structural parameters, $X_o$, and generating a corresponding initial covariance, $P_{X_o}$.

10. A method according to claim 9, wherein said initial estimate $X_o$ of said vector $X[q, r]$ is determined from a source of coarse structural information, said source being selected from the group consisting of topology databases, parameter databases, molecular primary structure databases, distance geometry calculations, simulated annealing calculations, restrained molecular dynamics calculations, amino acid sequence/primary structure databases, amino acid helical location data, and combinations thereof.

11. A method according to claim 1, wherein said method further includes $Y^{obs} = (Y_{1,1}^{obs}, Y_{1,2}^{obs}, \ldots Y_{2,1}^{obs}, Y_{2,2}^{obs}, \ldots Y_{K,J}^{obs})$, representative of each of said sets of observed data, an element of which set is represented as $Y_{k,j}^{obs}$, k being an index integer representing different points in time, for all k=1 to K, K being an integer representative of the number of sets of contemporaneous observed data elements, j being an index integer corresponding to the $j^{th}$ observed data element, for all j=1 to J, J being an integer representative of the number of observed data elements in each contemporaneous data set.

12. A method according to claim 1, wherein said method further includes the step of providing a second analytical model $f(X[q, r], \zeta([q])$, $\zeta[q]$ being a multi-dimensional, Gaussian random vector representative of process noise which forces a dynamic time evolution of said vector of structural parameters $X[q, r]$, where $f(X[q, r], \zeta[q])$ defines one or more mathematical expressions, said expressions being collectively representative of the time evolution of said vector of structural parameters $X[q, r]$, where $X[k+1, r] = f(X[k, r], \zeta[k])$, $X[k+1, r]$ being said vector of structural parameters at a time point k+1, $X[k, r]$ being said vector of structural parameters at a time point k, and $\zeta[k]$ being said random vector at time point k.

13. A method according to claim 1, wherein $\hat{X}[q, r]$ is representative of a predicted vector, $X^*[q, r]$ is representative of an updated vector, where q and r are index integers, and said predicted vector $\hat{X}[k, j]$ is generated from an updated vector $X^*[k, j-1]$ of a next previous recursion step when $j \neq 1$, from said second analytical model $f(X^*[k-1, J], \zeta[k-1])$ of a next previous recursion step when j=1 and $k \neq 1$, and from said initial estimate of the structural parameters $X_o$ when j=1 and k=1.

14. A method according to claim 1, wherein said molecule includes N atoms, and said vector of structural parameters $X[q, r]$ includes a representation of the position of each of said N atoms with respect to a reference Cartesian coordinate system.

15. A method according to claim 14, wherein said integer n is 3N.

16. A method according to claim 1, wherein said sets of observed data are selected from the group consisting of covalent bond lengths, covalent bond angles, dihedral angles, inter-proton distances, and combinations thereof.

17. A method according to claim 1, wherein said sets of observed data are inter-proton distances, and said inter-proton distances are represented by NOE intensities, said NOE intensities being used directly in said step of generating an updated estimate of said structural parameters.

18. A method according to claim 1, wherein said sets of observed data are inter-proton distances, and said inter-proton distances are represented by values calculated from NOE intensities.

19. A method according to claim 1, wherein said step of generating an updated estimate of said structural parameters further includes the substeps of generating a predicted vector $\hat{X}[k, j]$, generating a predicted vector $Y_{k,j}^{calc}(\hat{X}[k, j])$, and generating covariances $\hat{P}_X[k, j]$, $\hat{P}_Y[k, j]$ and $\hat{P}_{XY}[k, j]$, between a first measurement signified by index j−1 and a second measurement signified by index j, both measurements being observed at time instant k, said substeps being expressed by:

$$\hat{X}[k, j] = X^*[k, j-1];$$

$$\hat{P}_X[k, j] = P_X^*[k, j-1];$$

$$Y_{k,j}^{calc}(X[k, j]) = E[g_{k,j}(X[k, j])];$$

$$\hat{P}_Y[k, j] = \text{Cov}[g_{k,j}(X[k, j])];$$

and, $$\hat{P}_{XY}[k, j] = \text{Cov}[X[k, j] \cdot g_{k,j}(X[k, j])],$$

where E[ ] is an expected value operator, and where Cov[ ] is a covariance matrix operator.

20. A method according to claim 1, wherein said substeps of generating an updated vector and associated updated covariance are expressed by:

$$X^*[k, j] = \hat{X}[k, j] + \left(\frac{\hat{P}_{XY}[k, j]}{Y[k, j]}\right) \cdot \left(Y_{k,j}^{obs} - Y_{k,j}^{calc}(\hat{X}[k, j])\right);$$

$$P_X^*[k, j] = \hat{P}_X[k, j] - \left(\frac{1}{Y[k, j]}\right) \hat{P}_{XY}[k, j] \cdot \hat{P}_{XY}^T[k, j]; \text{ and,}$$

$$Y(k, j) = \Xi_{\eta_{k,j}} + \hat{P}_Y[k, j].$$

21. A computer-assisted method for generating a representation of the three dimensional structure of a molecule, said representation being an n-dimensional vector of structural parameters $X[q, r] = (X_1[q, r], X_2[q, r], \ldots X_n[q, r])^T$, at an associated pair of index integers q and r, n being an integer, $X_i[q, r]$ being a structural parameter, said $X[q, r]$ having a statistical uncertainty, and a covariance matrix $P_X[q, r]$ representative of said statistical uncertainty of said vector of structural parameters, said molecule consisting of N atoms, N being an integer, comprising the steps of:

A. providing m sets of observed data, $Y^{obs} = (Y_{1,1}^{obs}, Y_{1,2}^{obs}, \ldots Y_{2,1}^{obs}, Y_{2,2}^{obs}, \ldots Y_{K,J}^{obs})$, m being an integer, an element of which set is represented as $Y_{k,j}^{obs}$, k being an index integer representing different points in time, for all k=1 to K, K being an integer representative of the number of sets of contemporaneous observed data elements, j being an index integer corresponding to the $j^{th}$ observed data element, for all j=1 to J, J being an integer representative of the number of observed data elements in each contemporaneous data set, each of said observed data elements $Y_{k,j}^{obs}$ being relatable to at least one of said structural parameters $X_i[q, r]$, and having an associated observation noise $\eta_{k,j}$;

B. providing a first analytical model $g_{q,r}(X[q, r])$, where $g_{q,r}(X[q, r])$ defines one or more mathematical expressions representative of the relationship of each observed data element $Y_{k,j}^{obs}$ to one or more of said structural parameters $X_i[q, r]$, and $g_{q,r}(X[q, r])$ is representative of a vector $Y_{q,r}^{calc}(X[q, r])$;

C. providing a second analytical model $f(X[q, r], \zeta[q])$, $\zeta[q]$ being a multi-dimensional, Gaussian random vector representative of process noise which forces a dynamic time evolution of said vector of structural parameters $X[q, r]$, where $f(X[q, r], \zeta[q])$ defines one or more mathematical expressions, said expressions being collectively representative of the time evolution of said vector of structural parameters $X[q, r]$, where $X[k+1, r] = f(X[k, r], \zeta[k])$, $X[k+1, r]$ being said vector of structural parameters at a time point k+1, $X[k, r]$ being said vector of structural parameters at a time point k, and $\zeta[k]$ being said random vector at time point k;

D. providing an initial estimate of said structural parameters $X_o$, and generating a corresponding initial covariance, $P_{X_o}$;

E. generating an updated estimate of said structural parameters $X[q, r]$, and corresponding updated covariance $P_X[q, r]$, representative of the statistical uncertainty of said updated structural parameters, by non-linear recursive filtering of each of said observed data elements $Y_{k,j}^{obs}$ with a non-linear recursive filter, utilizing a predicted vector $\hat{X}[q, r]$ and generating an updated vector $X^*[q, r]$, where q and r are index integers, and including the substeps of:

i. providing said observed data element $Y_{k,j}^{obs}$,
ii. generating a predicted vector $\hat{X}[k, j]$ from an updated vector $X^*[k, j-1]$ of a next previous recursion step when $j \neq 1$, and from said second analytical model $f(X^*[k-1, J], \zeta[k-1])$ of a next previous recursion step when j=1 and $k \neq 1$, and from said initial estimate of the structural parameters $X_o$ when j=1 and k=1;
iii. generating a predicted vector $Y_{k,j}^{calc}(\hat{X}[k,j])$ and covariances $\hat{P}_X[k, j]$, $\hat{P}_Y[k, j]$ and $\hat{P}_{XY}[k, j]$, corresponding to $\hat{X}[k, j]$ and $Y^{calc}(\hat{X}[k, j])$;
iv. evaluating a difference between $Y_{k,j}^{calc}(\hat{X}[k, j])$ and $Y_{k,j}^{obs}$, and using said difference and said covariances $\hat{P}_X[k, j]$, $\hat{P}_Y[k, j]$ and $\hat{P}_{XY}[k, j]$ to generate an updated vector of structural parameters $X^*[k, j]$ and associated covariance $P_X^*[k, j]$;

F. repeating step (E) for all j=1 through J and for all k=1 through K, to obtain $X^*[K, J]$, whereby $X^*[K, J]$ is representative of the three dimensional structure of said molecule.

22. A method according to claim 21, wherein said method further includes the step of excluding a plurality of elements of said covariances, prior to said difference evaluating substep, including the following substeps:

i. excluding a plurality of elements of said covariance matrix $P_X[q, r]$, said plurality of elements being representative of pairs of atoms having a center-to-center spacing of at least 10 Å;
ii. generating a correlation coefficient for each component of said matrix $P_{XY}[q, r]$;
iii. sorting said correlation coefficients into a plurality of categories, said categories being representative of a correlation range; and,
iv. excluding at least one pairing of said categories from subsequent matrix operations with $P_{XY}[q, r]$ matrix.

23. A method according to claim 22, wherein said predetermined distance d is 10 Å, and said plurality of categories defines a high correlation category, a medium correlation category and a low correlation category, and said excluding substep excludes low/low category pairings and low/medium category pairings.

24. A method according to claim 21, wherein said integer n is 3N.

25. A method according to claim 21, wherein said initial estimate $X_o$ of said vector $X[q, r]$ is determined from a source of coarse structural information, said source being selected from the group consisting of topology databases, parameter databases, molecular primary structure databases, distance geometry calculations, simulated annealing calculations, restrained molecular dynamics calculations, amino acid sequence/primary structure databases, amino acid helical location data, and combinations thereof.

26. A method according to claim 21, wherein said sets of observed data are selected from the group consisting or covalent bond lengths, covalent bond angles, dihedral angles, inter-proton distances, and combinations thereof.

27. A method according to claim 21, wherein said sets of observed data are inter-proton distances, and said inter-proton distances are represented by NOE intensities, said NOE intensities being used directly in said step of generating an updated estimate of said structural parameters $X[q, r]$.

28. A method according to claim 21, wherein said sets of observed data are inter-proton distances, and said inter-proton distances are represented by values calculated from NOE intensities.

29. A method according to claim 21, wherein said substeps of generating a predicted vector $\hat{X}[k, j]$, generating a predicted vector $Y_{k,j}{}^{calc}(\hat{X}[k, j])$, and generating covariances $\hat{P}_X[k, j]$, $\hat{P}_Y[k, j]$ and $\hat{P}_{XY}[k, j]$, between a first measurement signified by index j−1 and a second measurement signified by index j, both measurements being observed at time instant k, are expressed by:

$$\hat{X}[k,j] = X^*[k, j-1];$$

$$\hat{P}_X[k,j] = P_X^*[k, j-1];$$

$$Y_{k,j}{}^{calc}(X[k,j]) = E[g_{k,j}(X[k,j])];$$

$$\hat{P}_Y[k,j] = \text{Cov}[g_{k,j}(X[k,j])];$$

and, $$\hat{P}_{XY}[k,j] = \text{Cov}[X[k,j]; g_{k,j}(X[k,j])],$$

where $E[\ ]$ is an expected value operator, and where $\text{Cov}[\ ]$ is a covariance matrix operator.

30. A method according to claim 21, wherein said evaluating substep 21.E. iv. is expressed by:

$$X^*[k, j] = \hat{X}[k, j] + \left(\frac{\hat{P}_{XY}[k, j]}{\Upsilon[k, j]}\right) \cdot (Y_{k,j}^{obs} - Y_{k,j}^{calc}(\hat{X}[k, j]));$$

$$P_X^*[k, j] = \hat{P}_X[k, j] - \left(\frac{1}{\Upsilon[k, j]}\right) \hat{P}_{XY}[k, j] \cdot \hat{P}_{XY}^T[k, j]; \text{ and,}$$

$$\Upsilon(k, j) = \Xi_{\eta_{k,j}} + \hat{P}_Y[k, j].$$

31. A computer system for generating a representation of the three dimensional structure of a molecule, said representation being an n-dimensional vector of structural parameters $X[q, r] = (X_1[q, r], X_2[q, r], \ldots X_n[q, r])^T$, at an associated pair of index integers q and r, n being an integer, $X_1[q, r]$ being a structural parameter, said $X[q, r]$ having a statistical uncertainty, and a covariance matrix $P_X[q, r]$ representative of said statistical uncertainty of said vector of structural parameters, said molecule consisting of N atoms, N being an integer, comprising:

A. means for providing m sets of observed data, $Y^{obs} = (Y_{1,1}^{obs}, Y_{1,2}^{obs}, \ldots Y_{2,1}^{obs}, Y_{2,2}^{obs}, \ldots Y_{K,J}^{obs})$, m being an integer, an element of which set is represented as $Y_{k,j}^{obs}$, k being an index integer representing different points in time, for all k=1 to K, K being an integer representative of the number of sets of contemporaneous observed data elements, j being an index integer corresponding to the $j^{th}$ observed data element, for all j=1 to J, J being an integer representative of the number of observed data elements in each contemporaneous data set, each of said observed data elements $Y_{k,j}^{obs}$ being relatable to at least one of said structural parameters $X_1[q, r]$, and having an associated observation noise $\eta_{k,j}$;

B. means for providing a first analytical model $g_{q,r}(X[q, r])$, where $g_{q,r}(X[q, r])$ defines one or more mathematical expressions representative of the relationship of each observed data element $Y_{k,j}^{obs}$ to one or more of said structural parameters $X_1[q, r]$, and $g_{q,r}(X[q, r])$ is representative of a vector $Y_{q,r}^{calc}(X[q, r])$;

C. means for providing a second analytical model $f(X[q, r], \zeta[q])$, $\zeta[q]$ being a multi-dimensional, Gaussian random vector representative of process noise, where $f(X[q, r], \zeta[q])$ defines one or more mathematical expressions, said expressions being collectively representative of the time evolution of said vector of structural parameters $X[q, r]$, where $$X[k+1, r] = f(X[k, r], \zeta[k]),$$

$X[k+1, r]$ being said vector of structural parameters at a time point k+1, $X[k, r]$ being said vector of structural parameters at a time point k, and $\zeta[k]$ being said random vector at time point k;

D. means for providing an initial estimate of said structural parameters $X_o$, and generating a corresponding initial covariance, $\hat{P}_{X_o}$;

E. means for generating an updated estimate of said structural parameters $X[q, r]$, and corresponding updated covariance $P_X[q, r]$, representative of the statistical uncertainty of said updated structural parameters, by non-linear recursive filtering of each of said observed data elements $Y_{k,j}^{obs}$ with a non-linear recursive filter, utilizing a predicted vector $\hat{X}[q, r]$ and generating an updated vector $X^*[q, r]$, where q and r are index integers, and further including:

i. means for providing said observed data element $Y_{k,j}^{obs}$, ii. means for generating a predicted vector $\hat{X}[k, j]$ from an updated vector $X^*[k, j-1]$ of a next previous recursion step when j≠1, and from said second analytical model $f(X^*[k-1, J], \zeta[k-1])$ of a next previous recursion step when j=1 and k/1, and from said initial estimate of the structural parameters $X_o$ when j=1 and k=1;

iii. means for generating a predicted vector $Y^{calc}(\hat{X}[k, j])$ and covariances $\hat{P}_X[k, j]$, $\hat{P}_Y[k, j]$ and $\hat{P}_{XY}[k, j]$, corresponding to $\hat{X}[k, j]$ and $Y_{k,j}^{calc}(\hat{X}[k, j])$;

iv. means for evaluating a difference between $Y_{k,j}^{calc}(\hat{X}[k, j])$ and $Y_{k,j}^{obs}$, and using said difference and said covariances $\hat{P}_X[k, j]$, $\hat{P}_Y[k, j]$ and $\hat{P}_{XY}[k, j]$ to generate an updated vector of structural parameters $X^*[k, j]$ and associated covariance $\hat{P}_X^*[k, j]$;

F. means operative to perform said updated estimate generating means for all j=1 through J and for all k=1 through K, to obtain $X^*[K, J]$, whereby $X^*[K, J]$ is representative of the three dimensional structure of said molecule.

32. A system according to claim 31, wherein said system further includes means for excluding a plurality of elements of said covariances, prior to said difference evaluating means, comprising:

i. means for excluding a plurality of elements of said covariance matrix $P_X[q, r]$, said plurality of elements being representative of pairs of atoms having a center-to-center spacing of at least 10 Å;

ii. means for generating a correlation coefficient for each component of said matrix $P_{XY}[q, r]$;

iii. means for sorting said correlation coefficients into a plurality of categories, said categories being representative of a correlation range; and, iv. means for excluding at least one pairing of said categories from subsequent matrix operations with $P_{XY}[q, r]$ matrix.

33. A system according to claim 32, wherein said predetermined distance d is 10 Å, and said plurality of categories defines a high correlation category, a medium correlation category and a low correlation category, and said excluding means excludes low/low category pairings and low/medium category pairings.

34. A system according to claim 31, wherein said integer n is 3N.

35. A system according to claim 31, wherein said initial estimate $X_o$ of said vector $X[q, r]$ is determined from a source of coarse structural information, said source being selected from the group consisting of topology databases, parameter databases, molecular primary structure databases, distance geometry calculations, simulated annealing calculations, restrained molecular dynamics calculations, amino acid sequence/primary structure databases, amino acid helical location data, and combinations thereof.

36. A system according to claim 31, wherein said sets of observed data are selected from the group consisting of covalent bond lengths, covalent bond angles, dihedral angles, inter-proton distances, and combinations thereof.

37. A system according to claim 31, wherein said sets of observed data are inter-proton distances, and said inter-proton distances are represented by NOE intensities, said NOE intensities being used directly by said means for generating an updated estimate or said structural parameters X[q, r].

38. A system according to claim 31, wherein said sets of observed data are inter-proton distances, and said inter-proton distances arc represented by values calculated from NOE intensities.

39. A system according to claim 31, wherein said means for generating a predicted vector $\hat{X}[k, j]$, means for generating a predicted vector $Y^{calc}(\hat{X}[k,j])$, and means for generating covariances $\hat{P}_X[k, j]$, $\hat{P}_Y[k, j]$ and $\hat{P}_{XY}[k, j]$, between a first measurement signified by index j−1 and a second measurement signified by index j, both measurements being observed at time instant k, are expressed by:

$\hat{X}[k, j] = X^*[k, j-1]$;

$\hat{P}_X[k, j] = P_X^*[k, j-1]$;

$Y_{k, j}^{calc}(X[k, j]) = E[g_{k, j}(X[k, j])]$;

$\hat{P}_Y[k, j] = Cov[g_{k, j}(X[k, j])]$;

and, $\hat{P}_{XY}[k, j] = Cov[X[k, j], g_{k, j}(X[k, j])]$, where E[] is an expected value operator, and where Cov[] is a covariance matrix operator.

40. A system according to claim 31, wherein said evaluating means 31. E. iv. is expressed by:

$$X^*[k, j] = \hat{X}[k, j] + \left(\frac{\hat{P}_{XY}[k, j]}{Y[k, j]}\right) \cdot \left(Y_{k,j}^{obs} - Y_{k,j}^{calc}(\hat{X}[k, j])\right);$$

$$P_X^*[k, j] = \hat{P}_X[k, j] - \left(\frac{1}{Y[k, j]}\right)\hat{P}_{XY}[k, j] \cdot \hat{P}_{XY}^T[k, j]; \text{ and,}$$

$$Y(k, j) = \Xi_{\eta_{k,j}} + \hat{P}_Y[k, j].$$

* * * * *